United States Patent [19]

Kathawala

[11] 4,085,149
[45] Apr. 18, 1978

[54] α-ALKYL-P-PHENOXY BENZYL ALCOHOLS

[75] Inventor: Faizulla G. Kathawala, West Orange, N.J.

[73] Assignee: Sandoz, Inc., E. Hanover, N.J.

[21] Appl. No.: 662,125

[22] Filed: Feb. 27, 1976

Related U.S. Application Data

[60] Division of Ser. No. 510,477, Sep. 30, 1974, Pat. No. 3,962,459, which is a continuation-in-part of Ser. No. 394,181, Sep. 4, 1973, abandoned.

[51] Int. Cl.$^2$ .............................................. C07C 43/20
[52] U.S. Cl. .................................................. 260/613 R
[58] Field of Search .................................... 260/613 R

[56] References Cited

U.S. PATENT DOCUMENTS 3,962,459  6/1976  Kathawala ...................... 260/592 X

OTHER PUBLICATIONS

Mowry et al., J.A.C.S., vol. 68 (1946) pp. 1105–1109.

Farnum et al., Proc. N. Dak. Acad. of Sci., vol. 20 (1966) pp. 78–81.

Primary Examiner—Bernard Helfin
Attorney, Agent, or Firm—Gerald D. Sharkin; Richard E. Vila; Joseph J. Borovian

[57] ABSTRACT

Hypolipidemic agents of the formula:

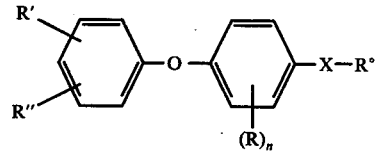

wherein
  X is C=O or CHOH,
  R° is branched lower alkyl,
  R is hydrogen, alkyl, or halo,
  n is 1 or 2, and
  R' and R'' are hydrogen, halo, alkyl or alkoxy, e.g., 4-phenoxy-pivalophenone.

7 Claims, No Drawings

α-ALKYL-P-PHENOXY BENZYL ALCOHOLS

This application is a divisional of application Ser. No. 510,477, filed Sept. 30, 1974, now issued as U.S. Pat. No. 3,962,459, which application is a continuation-in-part of application Ser. No. 394,181, filed Sept. 4, 1973, now abandoned. This application is a continuation-in-part of copending application Serial No. 394,181, filed September 4, 1973.

The compound 4-phenoxy-pivalophenone has been previously disclosed in the literature by D. S. Tarbell et al. J.A.C.S. 65, 2169–74 (1943). The compound 2-methyl-4'-phenoxypropiophenone has been described by Buu Hoi et al., J.C.S. 1954, 1034–38. In addition, the compound 4'-methoxy-4-phenoxyisovalerophenone has been described by Petit and Buu Hoi, J. Org. Chem. 26, 3834 (1961). Furthermore, the compound 4-methyl-4'-phenoxy-valerophenone has been described by Tomita and Watamaba, J. Pharm. Soc. Japan 71, 1198–1203 (1951). To my knowledge no pharmacological activity has been heretofore associated with any of these compounds.

The present invention involves the novel use of the compounds of the formula I:

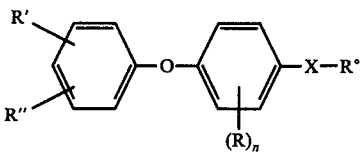

wherein
X is C=O or CHOH,
R° is branched alkyl of 3 to 5 carbon atoms, preferably tertiary branched alkyl, e.g., t-butyl,
R is hydrogen, alkyl of 1 to 4 carbon atoms, or halo of atomic weight of from 18 to 36,
n is 1 or 2,
R' is hydrogen, halo of atomic weight of from 18 to 36, alkyl of 1 to 4 carbon atoms or alkoxy of 1 to 4 carbon atoms, and
R" is hydrogen, halo of atomic weight of from 18 to 36, alkyl of 1 to 4 carbon atoms or alkoxy of 1 to 4 carbon atoms.

The preferred compounds of formula I are those in which R, R' and R" are hydrogen, and those in which R° is tert. butyl, the most preferred compound being 4-phenoxypivalophenone.

The invention further provides the novel compounds of formula Ia:

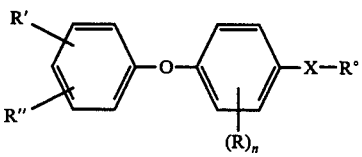

wherein
R°, R, R', R" and X have the same significance as defined above, provided that
(i) when R, R' and R" each signifies hydrogen, then R° signifies other than —C(CH$_3$)$_3$,
(ii) when R, R' and R" each signifies hydrogen and X signifies C=O, then R° signifies other than —CH(CH$_3$)$_2$ or —(CH$_2$)$_2$CH(CH$_3$)$_2$, and
(iii) when one of R' and R" signifies CH$_3$O— in the 4-position and the other signifies hydrogen, and R signifies hydrogen and X signifies C=O, then R° signifies other than —CH$_2$CH(CH$_3$)$_2$.

The compounds of the formula I wherein X is C=O may be prepared in a Step A reaction by reacting a compound of the formula II:

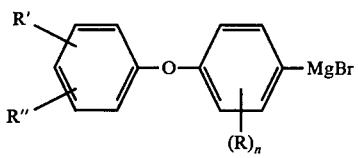

in which R, n, R' and R" are as defined, with a compound of the formula III:

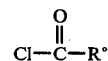

$$Cl-\overset{\overset{O}{\|}}{C}-R°$$

in which R° is as defined above, and hydrolyzing the resulting product.

The reaction of Step A may be carried out at temperatures in the range of from 0° C. to 100° C. The reaction is conveniently carried out in the presence of an inert organic solvent of conventional type including the cyclic and acyclic ethers, such as diethyl ether and tetrahydrofuran.

In Step A, the hydrolysis may be effected under alkaline, neutral or acid conditions, preferably mild acidic conditions, suitably using hydrochloric or sulfuric acid, preferably hydrochloric acid. The hydrolysis may be carried out conveniently at a temperature of from −40° to 100° C., preferably at a temperature of from 10° to 30° C.

The compounds of the formula I wherein X is CHOH may be prepared in a Step B reaction by reducing the carbonyl group of a compound produced by the Step A reaction in a known manner. The reaction of Step B is suitably carried out at temperatures in the range of 0° C. to 100° C. employing a reducing agent of known type such as sodium borohydride, lithium aluminum hydride, diborane and the like, preferably sodium borohydride. The reaction is conducted in the presence of an inert organic solvent of known type, such as ethanol, isopropanol, diethyl ether, tetrahydrofuran and the like. The resulting compounds of formula I may be isolated and purified by conventional techniques.

The compounds of the formula II may be prepared in a reaction Step 1 involving the reaction of a compound of the formula IV:

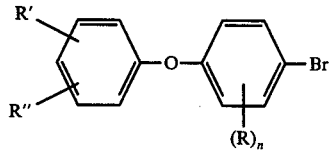

in which R, n, R' and R" are as defined, with magnesium in a conventional manner for preparation of a Grignard compound from the corresponding bromo compound.

The compounds of the formula III and IV are both either known or may be prepared in a known manner from known materials.

The compounds of structural formulae I are useful because they possess pharmacological activity in animals. In particular, the compounds are useful as hypolipidemic agents, particularly hypolipoproteinemic agents, as evidenced, for example, by lowering cholesterol and triglyceride blood serum levels in tests on a group of white rats which are given typically 30–250 milligrams per kilogram of body weight per diem of the compound orally, for 6 days, followed by extraction with isopropanol of serum or plasma after anesthetizing the rats with sodium hexobarbital, and then noting the cholesterol and triglyceride contents as compared to those of a control group. The cholesterol and triglyceride contents are determined by the methods described by Lofland, H.B., Anal. Biochem. 9:393 (1964): (Technicon method N 24a): and G. Kessler and H. Lederer, Technicon Symposium, Mediad Inc., New York, pages 345–347 (1965), respectively. For such usage, the compounds may be administered orally or parenterally, preferably orally, and in admixture with conventional pharmaceutical carriers. The dosage administered may vary depending upon known variables such as the particular compound employed and the severity of the condition being treated. In general, satisfactory results are obtained when administered at a daily dosage of from about 4 milligrams to about 250 milligrams per kilogram of animal body weight, preferably given orally and in divided doses, 2 to 4 times a day, or in sustained release form. For most mammals the total daily dosage is from about 200 milligrams to about 3000 milligrams of the compound, and dosage forms suitable for internal administration comprise from about 50 to 1500 milligrams of the compound in admixture with a solid or liquid pharmaceutically acceptable carrier or diluent.

For above usage, the compounds of formula I may be administered orally in such forms as tablets, dispersible powders, granules, capsules, syrups and elixirs; and parenterally as solutions, suspensions, dispersions, emulsions, and the like, e.g., a sterile injectable solution such as an aqueous suspension. These pharmaceutical preparations may contain 0.5% up to about 90% of the active ingredient in combination with the carrier or adjuvant, more usually between 3% and 50% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert liquid or solid diluent, e.g., calcium carbonate, calcium phosphate, kaolin, peanut oil, sesame oil and corn oil.

Capsules containing the ingredients indicated below may be prepared by conventional techniques and are useful in treating lipidemia, particularly hyperlipoproteinemia, in mammals at a dose of one capsule 2 to 4 times a day.

| Ingredients | Weight (mg.) |
|---|---|
| 4-phenoxy-pivalophenone | 100 |
| Peanut or sesame oil | 120 |

The following examples are for purposes of illustration only.

EXAMPLE 1

4-phenoxy-pivalophenone

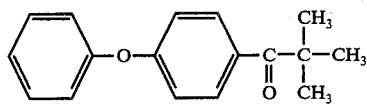

To a flask containing 33.6 g. of magnesium and crystals of iodine, is added 50–70 ml. of a solution of 300 g. of (p-bromophenyl) phenyl ether in 500 ml. of tetrahydrofuran. The remainder of the solution is added as needed to maintain a gentle reflux and the resulting mixture heated to reflux for 30 minutes. The resulting mixture is then added to a solution of trimethylacetyl chloride in 500 ml of tetrahydrofuran at a rate to maintain 40°–50° C. The resulting mixture is then stirred at ambient temperature for one hour and then 200 ml. of 2N. hydrochloric acid is added. The organic layer is washed twice with one liter of 2N. sodium carbonate solution, dried and evaporated in vacuo to a liquid weighing about 290 g. This liquid is distilled under reduced pressure to obtain 4-phenoxypivalophenone, b.p. 136°–139° C. at 0.1 mm/Hg. This product may also be named 2,2-dimethyl-4'-phenoxy-propiophenone.

EXAMPLE 2

Following the procedure of Example 1, but employing appropriate starting materials in approximately equivalent amounts, the following additional compounds are prepared:

(A) 4-(m-chlorophenoxy)-pivalophenone,
(B) 2-methyl-4'-phenoxy-propiophenone, b.p. 130°–135° C. at 0.2 mm/Hg.,
(C) 4-(p-methoxyphenoxy)-3,5-dichloropivalophenone, m.p. 63°–65° C.,
(D) 4-(p-methoxyphenoxy)-3-chloropivalophenone, m.p. 59°–60° C.,
(E) 4-(p-methoxyphenoxy)-pivalophenone, m.p. 78°–81° C.,
(F) 4-phenoxy-3-methyl-pivalophenone,
(G) 4-(p-methylphenoxy)-pivalophenone,
(H) 4-(3'-chloro-4'-methoxyphenoxy)3,5-dichloropivalophenone, m.p. 76°–79° C.,
(I) 4-(3',5'-di-t-butylphenoxy)-pivalophenone, m.p. 70°–85° C.,
(J) 4-(p-chlorophenoxy)-pivalophenone, m.p. 60°–62° C.,
(K) 4-phenoxy-3,5-dichloro-pivalophenone, (L) 3,3-dimethyl-4'-phenoxy-butyrophenone, m.p. 32°-34° C.,
(M) 4-(p-fluorophenoxy)-pivalophenone,
(N) 4-methyl-4'-phenoxy-valerophenone, and
(O) 4'-methoxy-4-phenoxyisovalerophenone.

EXAMPLE 3

α-tert.-butyl-p-phenoxy benzyl alcohol

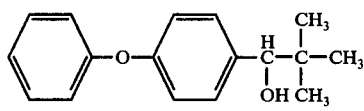

To a solution of 25.4 g. of 4-phenoxy-pivalophenone in 250 ml. of isopropanol is added 5.0 g. of sodium borohydride. The resulting mixture is stirred at ambient temperature for 2 hours, evaporated in vacuo and the residue extracted with water and with ether. The organic phase is evaporated in vacuo to a clear oil which crystallizes on standing to yield α-tert.-butyl-p-phenoxy benzyl alcohol, m.p. 79°-80° C.

EXAMPLE 4

Following the procedure of Example 3, but employing appropriate starting materials in approximately equivalent amounts, the following additional compounds are prepared:

(A) α-isopropyl-p-phenoxy benzyl alcohol,
(B) αa-tert.-butyl-p-(p-methoxyphenoxy) benzyl alcohol, m.p. 44°-46° C.,
(C) α-tert.-butyl-p-(m-chlorophenoxy) benzyl alcohol,
(D) α-tert.-butyl-p-phenoxy-m,m-dichloro benzyl alcohol,
(E) α-tert.-butyl-p-(p-chlorophenoxy) benzyl alcohol, m.p. 64°-67° C.
(F) α-tert.-butyl-p-(3',5'-di-tert.-butylphenoxy) benzyl alcohol, m.p. 104°-106° C.
(G) α-tert.-butyl-p-(p-methylphenoxy) benzyl alcohol, m.p. 58°-61° C.,
(H) α-tert.-butyl-p-(p-fluorophenoxy) benzyl alcohol, m.p. 55°-59° C.,
(I) α-tert.-butyl-m,m-dichloro-p-(p-methoxyphenoxy) benzyl alcohol,
(J) α-tert.-butyl-m-chloro-p-(p-methoxyphenoxy) benzyl alcohol,
(K) α-tert.-butyl-m-methyl-p-phenoxy benzyl alcohol,
(L) α-tert.-butyl-m,m-dichloro-p-(m-chloro-p-methoxy) benzyl alcohol,
(M) α-isopentyl-p-phenoxy benzyl alcohol, and
(N) α-isobutyl-p-(p-methoxyphenoxy) benzyl alcohol.

What is claimed is:
1. A compound of the formula:

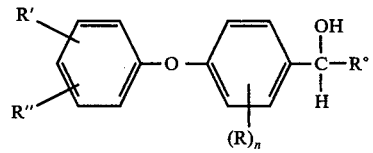

wherein:
R° is branched alkyl of 3 to 5 carbon atoms,
R is hydrogen, alkyl of 1 to 4 carbon atoms or halo of atomic weight of from 18 to 36,
$n$ is 1 or 2,
R' is hydrogen, alkyl of 1 to 4 carbon atoms, halo of atomic weight of from 18 to 36 or alkoxy of 1 to 4 carbon atoms, and
R" is hydrogen, alkyl of 1 to 4 carbon atoms, halo of atomic weight of from 18 to 36 or alkoxy of 1 to 4 carbon atoms,
provided that when R, R' and R" each signifies hydrogen, then R° signifies other than —C(CH$_3$)$_3$.

2. The compound which is α-tert.-butyl-p-phenoxy benzyl alcohol.

3. The compound of claim 1 which is α-tert.-butyl-p-(p-methoxyphenoxy) benzyl alcohol.

4. The compound of claim 1 which is α-tert.-butyl-p-(p-chlorophenoxy) benzyl alcohol.

5. The compound of claim 1 which is α-tert.-butyl-p-(3',5'-di-tert.-butylphenoxy) benzyl alcohol.

6. The compound of claim 1 which is α-tert.-butyl-p-(p-methylphenoxy) benzyl alcohol.

7. The compound of claim 1 which is α-tert.-butyl-p-(p-fluorophenoxy) benzyl alcohol.

* * * * *